United States Patent
Stroefer et al.

(10) Patent No.: US 7,273,955 B2
(45) Date of Patent: Sep. 25, 2007

(54) METHOD FOR THERMAL STABILIZATION OF HIGHLY CONCENTRATED FORMALDEHYDE SOLUTIONS

(75) Inventors: Eckard Stroefer, Mannheim (DE); Thomas Grützner, Stuttgart (DE); Hans Hasse, Kaiserslautern (DE)

(73) Assignee: BASF Aktiengesellschaft (DE)

( * ) Notice: Subject to any disclaimer, the term of this patent is extended or adjusted under 35 U.S.C. 154(b) by 145 days.

(21) Appl. No.: 10/547,857

(22) PCT Filed: Mar. 4, 2004

(86) PCT No.: PCT/EP2004/002181

§ 371 (c)(1),
(2), (4) Date: Sep. 2, 2005

(87) PCT Pub. No.: WO2004/078691

PCT Pub. Date: Sep. 16, 2004

(65) Prior Publication Data

US 2006/0084827 A1    Apr. 20, 2006

(30) Foreign Application Priority Data

May 4, 2003  (DE) ................................ 103 09 286

(51) Int. Cl.
*C07C 47/00* (2006.01)
(52) U.S. Cl. ..................................................... 568/422
(58) Field of Classification Search ................. 568/422
See application file for complete search history.

(56) References Cited

U.S. PATENT DOCUMENTS

| 2,440,732 | A |   | 5/1948 | Yates |               |
|-----------|---|---|--------|-------|---------------|
| 4,085,079 | A | * | 4/1978 | Kmetz et al. | 260/29.6 |
| 4,247,487 | A | * | 1/1981 | Percy | 568/422 |
| 4,289,912 | A | * | 9/1981 | Harris et al. | 568/422 |
| 4,390,727 | A | * | 6/1983 | De Micheli et al. | 568/422 |
| 5,912,389 | A | * | 6/1999 | Matsumoto | 568/422 |
| 6,610,888 | B1 |  | 8/2003 | Ströfer et al. | |
| 2005/0040359 | A1 | | 2/2005 | Ströfer | |

FOREIGN PATENT DOCUMENTS

| DE | 101 54 187 | 5/2003 |
| DE | 101 58 813 | 6/2003 |
| EP | 1 063 221 | 12/2000 |
| GB | 1190682 | 5/1970 |

* cited by examiner

*Primary Examiner*—Sikarl A. Witherspoon
(74) *Attorney, Agent, or Firm*—Connolly Bove Lodge & Hutz

(57) ABSTRACT

Method of stabilizing high-concentration formaldehyde solutions having a $CH_2O$ content of >70% by weight against precipitation of solids, which comprises heating the high-concentration formaldehyde solution at a heating rate of at least 5° C./min to a temperature of from 80° C. to 200° C. immediately after it has been prepared and storing it at a temperature in this range.

10 Claims, 2 Drawing Sheets

METHOD FOR THERMAL STABILIZATION OF HIGHLY CONCENTRATED FORMALDEHYDE SOLUTIONS

RELATED APPLICATIONS

This application is a national stage application (under 35 U.S.C. 371) of PCT/EP2004/002181 filed Mar. 4, 2004 which claims benefit to German application 103 09 286.2 filed Mar. 4, 2003.

The present invention relates to a method of stabilizing high-concentration formaldehyde solutions against precipitation of solids.

Formaldehyde is an important industrial chemical and is used to produce numerous industrial products and consumer articles. Over 50 branches of industry at present make use of formaldehyde, essentially in the form of aqueous solutions or formaldehyde-containing synthetic resins. Commercially available aqueous formaldehyde solutions have total concentrations of from 20 to 55% by weight of formaldehyde in the form of monomeric formaldehyde, methylene glycol and oligomeric polyoxymethylene glycols.

Water, monomeric (free) formaldehyde, methylene glycol and oligomeric polyoxymethylene glycols having various chain lengths are present together in aqueous solutions in a thermodynamic equilibrium which is characterized by a particular distribution of polyoxymethylene glycols of differing lengths. The term "aqueous formaldehyde solution" also refers to formaldehyde solutions in which virtually no free water is present and water is present essentially only in chemically bound form as methylene glycol or in the terminal OH groups of the polyoxymethylene glycols. This is particularly true of concentrated formaldehyde solutions. Polyoxymethylene glycols can have, for example, from 2 to 9 oxymethylene units. Thus, dioxymethylene glycol, trioxymethylene glycol, tetraoxymethylene glycol, pentaoxymethylene glycol, hexaoxymethylene glycol, heptaoxymethylene glycol, octaoxymethylene glycol and nonaoxymethylene glycol can be present together in aqueous formaldehyde solutions. The distribution is concentration-dependent. Thus, the maximum of the distribution in dilute formaldehyde solutions corresponds to homologues having a short chain length, while in more concentrated formaldehyde solutions it corresponds to homologues having a greater chain length. A shift in the equilibrium toward longer-chain (higher molecular weight) polyoxymethylene glycols can be brought about by removal of water, for example by distillation with a superimposed condensation reaction in a film evaporator. The establishment of equilibrium in this case occurs at a finite rate by intermolecular condensation of methylene glycol and low molecular weight polyoxymethylene glycols with elimination of water to form higher molecular weight polyoxymethylene glycols.

However, the high-concentration formaldehyde solutions obtained by removal of water are unstable in the sense that precipitation of solids occurs after a certain time. The precipitated solids are essentially the above-described longer-chain formaldehyde oligomers or polyoxymethylene glycols. Stabilization of the high-concentration formaldehyde solutions so as to prevent precipitation of solids can be achieved by addition of stabilizers, for example methanol. However, the presence of stabilizers is frequently undesirable in the further use of the high-concentration formaldehyde solutions.

It is known that moderately concentrated formaldehyde solutions having $CH_2O$ contents of up to about 50% by weight can be mixed with about 0.2-2% by weight of methanol as stabilizer and be stored at about 55° C. to avoid precipitation of solids. More highly concentrated formaldehyde solutions having a $CH_2O$ content of >70% by weight, for example about 80% by weight, initially consist of a single phase after their preparation at low temperatures of about 20-50° C. However, precipitation of solids occurs after a certain time. The cause appears to be the slow growth of the polyoxymethylene glycol chains in the formaldehyde solution until the solubility limit is exceeded.

It is an object of the present invention to provide a method of stabilizing high-concentration formaldehyde solutions against precipitation of solids.

We have found that this object is achieved by a method of stabilizing high-concentration formaldehyde solutions having a $CH_2O$ content of >70% by weight against precipitation of solids, which comprises heating the high-concentration formaldehyde solution at a heating rate of at least 5° C./min to a temperature of from 80° C. to 200° C. immediately after it has been prepared and storing it at a temperature in this range.

Although it is known that the solubility of formaldehyde increases in water at higher temperatures, heating such high-concentration formaldehyde solutions for the purpose of stabilization has hitherto been ruled out. This is because of the prevailing opinion that the rate of the condensation reaction and thus the rate of growth of the polyoxymethylene glycols increases at higher temperatures and premature precipitation of solids will occur as a result. It is therefore especially surprising that high-concentration formaldehyde solutions can nevertheless be thermally stabilized.

The high-concentration formaldehyde solution is heated at a heating rate of at least 5° C./min to a temperature of from 80° C. to 200° C. immediately after it has been prepared and is stored at a temperature in this range. When a temperature of at least 80° C. has been reached, heating can be continued at a lower heating rate or else the formaldehyde solution can be left at the temperature reached. It can also be cooled from a higher temperature which has been reached to a lower temperature, as long as the temperature does not drop below 80° C. for a prolonged period. Furthermore, it is important that a temperature of 200° C. is not significantly exceeded. This is because degradation reactions can occur in the high-concentration formaldehyde solution, for example by means of Cannizzaro disproportionation or decomposition to CO and $H_2$, at higher temperatures.

"Immediately after it has been prepared" means that the high-concentration formaldehyde solution obtained at, for example, from 20 to 60° C. is heated at the specified heating rate after not more than 60 minutes, preferably after not more than 5 minutes.

The concentration of the formaldehyde solution can be >70% by weight, >75% by weight or even >80% by weight, of $CH_2O$. Formaldehyde solutions of this concentration can be obtained by any methods, but they are preferably obtained by distillation. Particular preference is given to using processes as described in EP-A 1 063 221 and in the German patent application DE 101 54 187.2, which is not a prior publication.

The heating rate is preferably at least 10° C./min. A heating rate of at least 10° C./min is preferred particularly when the pH of the solution is less than 3 or greater than 6. The solution is preferably heated at the specified heating rate to at least 90° C., particularly preferably at least 100° C., and the temperature subsequently does not go below this value. The final temperature is preferably not more than 150° C., particularly preferably not more than 135° C.

The pH of the high-concentration formaldehyde solution is usually in the range from 1 to 10, preferably from 2 to 9, particularly preferably from 3 to 6. The pH can be brought into the desired range by addition of buffer substances, for example a formate buffer.

The rapid heating according to the present invention of the high-concentration formaldehyde solutions can be carried out in any open or closed systems. Examples of suitable apparatuses are stirred vessels which can be heated by means of jackets or coiled tubes (internal or external). Apparatuses having heat exchanger characteristics, e.g. shell-and-tube heat exchangers, plate apparatuses or helically bound tubes, are particularly preferred. These can be operated in cocurrent, countercurrent or cross-current. Heating can be carried out by means of any media, for example using condensing steam or by means of single-phase liquids or gases. The abovementioned apparatuses can be readily designed and operated so that the required heating rate is obtained.

After heating, the high-concentration formaldehyde solution can be stored in any open or closed systems. For the purposes of the present invention, "storage" constitutes leaving the high-concentration formaldehyde solution in the temperature window from 80 to 200° C. for a certain period of time. This period of time can be very short, for example only a few minutes may elapse until the high-concentration formaldehyde solution is used in a chemical reaction. However, the period of time can also be very long, for example days, weeks or months. The solution is preferably stored in a simple vessel having an internal heat exchanger. The solution can also be dispensed into drums, containers or tank cars and dispatched, with the temperature having to be maintained at $\geq 80°$ C. during transport.

Figure 1:
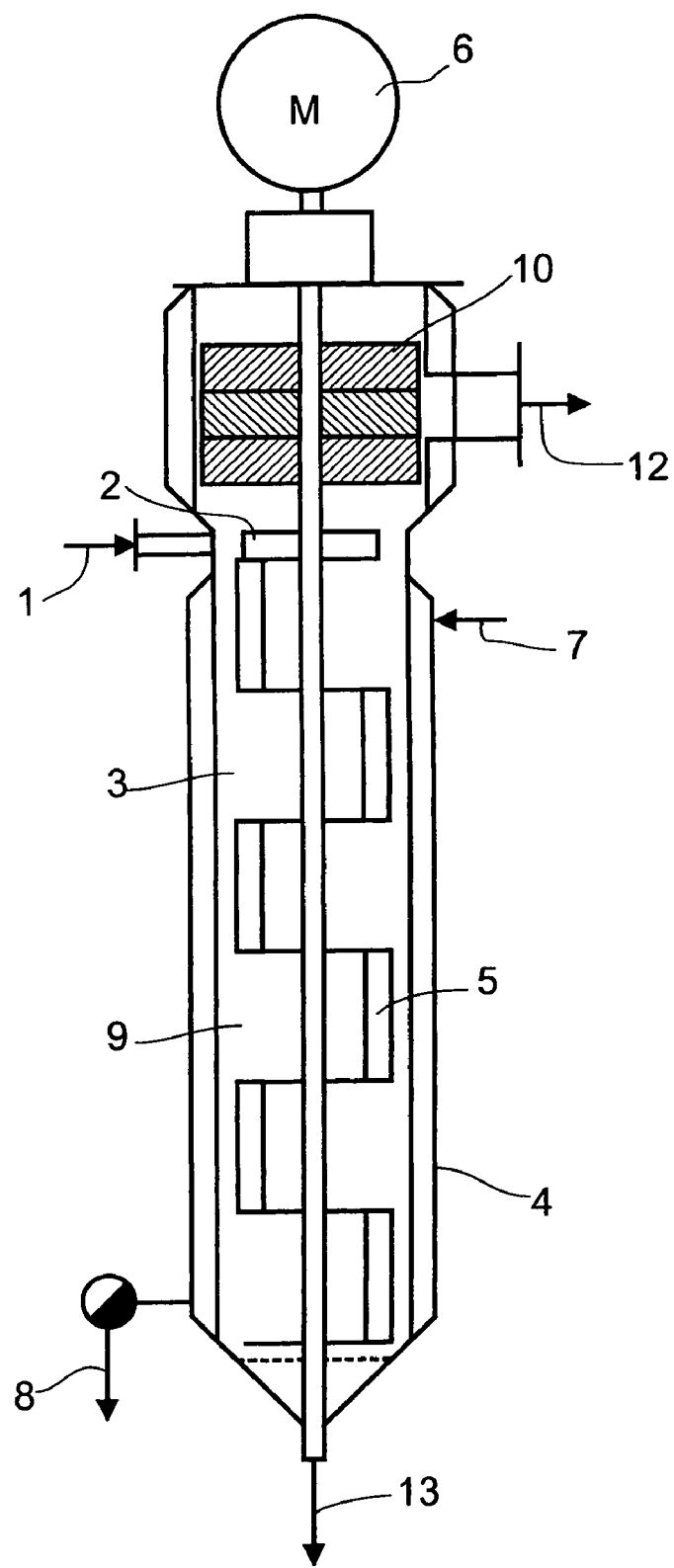
FIG. 1 depicts a film evaporator suitable for preparing high-concentration formaldehyde solutions.

The high-concentration formaldehyde solutions are preferably prepared in a film evaporator or a helical tube evaporator. One suitable film evaporator is shown in FIG. 1. This is a thin film evaporator. The feed 1, consisting of raw solution (starting material mixture) and, if desired, a recycle stream, is firstly fed to a liquid distributor 2. This distributes the raw solution over an evaporation surface 3. The evaporation surface 3 (heat-exchange surface) usually has a cylindrical shape, but can also be at least partly conical. It is in thermal contact with the inside of a heating jacket 4 which supplies heat to the evaporation surface 3. The liquid distributor 2 contributes to the feed solution being uniformly distributed over the circumference of the evaporation surface 3.

Rotating wiper blades 5 then distribute the solution further over the evaporation surface 3, ensure maintenance and transport of a liquid film on the evaporation surface 3 and contribute to intensification of heat and mass transfer in the liquid. These wiper blades 5 are driven by a drive device 6. Depending on the configuration and positioning of the wiper blades 5, the liquid film can be kept thin or can be banked up. It is in this way possible to alter the residence time or the residence time distribution of the solution in the film evaporator. The typical residence time of the solution in the film evaporator is from 1 s to 10 min, preferably from 2 s to 2 min.

A heating medium, e.g. steam, is fed into the heating jacket through a heating medium inlet 7. This heating medium heats the evaporation surface. Cooled heating medium, e.g. condensed water in the case of steam as heating medium, is discharged via the heating medium outlet 8.

As a result of the supply of heat to the evaporation surface 3, part of the solution fed to the film evaporator is vaporized, as a result of which the composition of the part of the solution which has not been vaporized is altered.

The vapor formed (i.e. vaporized liquid or gases) goes into a phase separation space 9 and from there into a droplet precipitator 10. Here, liquid droplets entrained in the vapor are removed from the gas phase and returned to the liquid (solution). The concentrate 13 is discharged in a suitable way from the phase separation space 9, while the vapor 12 is taken off from the droplet precipitator 10. The vapor is introduced into a condenser (not shown) where it is at least partly condensed to give a condensate.

If an aqueous formaldehyde solution is introduced into the film evaporator described, the liquid 13 becomes enriched in the polyoxymethylene glycols, while the condensate from the vapor 12 is low in polyoxymethylene glycols and rich in formaldehyde and methylene glycol. In this way, two fractions, viz. concentrate 13 and (partial) condensate from the vapor 12, which are selectively enriched in particular components of the raw solution 1 originally fed in are obtained.

In a particular embodiment, the condenser can be integrated into the body of the evaporator, which results in a shorter residence time of the vaporized components in the vapor phase and also a more compact construction.

Suitable operating conditions for the film evaporator are generally a temperature of from 10° C. to 200° C., preferably from 50° C. to 150° C., at an absolute pressure of from 0.5 mbar to 2 bar, preferably from 30 mbar to 1.5 bar, particularly preferably from 60 mbar to 1.0 bar. The temperature of the high-concentration formaldehyde solution leaving the film evaporator as bottom product is usually from 20 to 60° C.

Apart from the embodiment of a film evaporator shown in FIG. 1, it is also possible to use an apparatus without any mechanical influence on the liquid film present on the evaporation surface. The heat-transfer surface of such a falling film evaporator or falling stream evaporator can be configured as tubes or plates.

Figure 2:
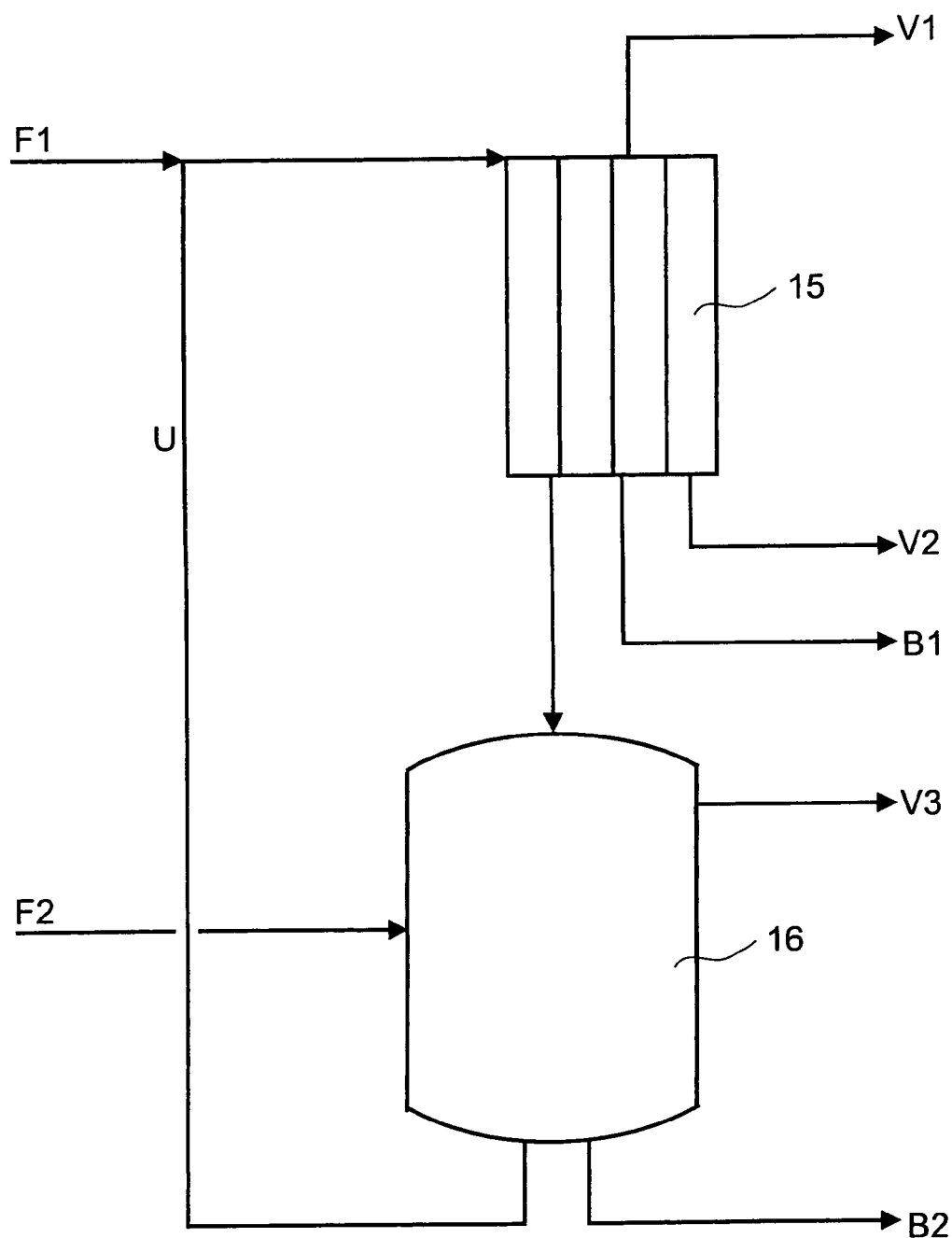
FIG. 2 depicts possible modes of operation of a film evaporator according to the invention.

Depending on the specific process requirements, a film evaporator can be operated in various ways. FIG. 2 schematically shows the possible modes of operation. Here, the actual film evaporator is labeled 15 and a vapor separator (i.e. phase separation space with droplet precipitator) is labeled 16. Both the film evaporator 15 and the vapor separator 16 can be different from the specific type of construction shown in FIG. 1 and can have further inlets and outlets in addition to those shown in FIG. 1. V1, V2 and V3 denote vapor streams; all other streams are usually liquid.

The film evaporator 15 can be operated in a single pass in respect of the unvaporized liquid leaving the evaporator or can be operated in the circulation mode. The liquid circuit U is technically necessary for operation in the circulation mode.

The following table shows the active streams for each of the possible modes of operation.

| | F1 | F2 | B1 | B2 | V1 | V2 | V3 | U |
|---|---|---|---|---|---|---|---|---|
| Single pass, vapor and liquid in countercurrent | X | | X | | X | | | |
| Single pass, vapor and liquid in cocurrent | X | | X | | | X | | |
| Circulation mode, feed into liquid circuit, vapor and liquid in cocurrent | X | | | X | | X | | X |

-continued

|  | F1 | F2 | B1 | B2 | V1 | V2 | V3 | U |
|---|---|---|---|---|---|---|---|---|
| Circulation mode, feed into liquid circuit, vapor and liquid in countercurrent | X |  | X | X |  |  |  | X |
| Circulation mode, feed into vapor separator, vapor and liquid in cocurrent |  | X | (X) | X |  | X | (X) | X |
| Circulation mode, feed into vapor separator, vapor and liquid in counter current |  | X |  | X | X |  | (X) | X |

The film evaporator can have side offtakes at suitable points, so that liquid fractions having a particular degree of enrichment can be taken off via these side offtakes. It is also possible for a plurality of evaporators to be connected in series to form an evaporator cascade in which the liquid, concentrated outflow from one evaporator forms, if desired after a side stream has been taken off, the feed to the next evaporator of the evaporator cascade.

The high-concentration formaldehyde solutions obtained are stabilized according to the present invention, for example in one of the abovementioned apparatuses, and can, after storage, be used for a large number of chemical reactions. Examples of such reactions are:

propynol, and the reaction of acetylene with formaldehyde solution in a Reppe reaction to form butynediol which can be hydrogenated to give butanediol;

aldolization reactions of formaldehyde with itself or with higher aldehydes to form polyhydric alcohols and sugars, pentaerythritol, trimethylolpropane and neopentyl glycol;

the reaction of formaldehyde and CO to give glycolic acid;

the preparation of chelating substances such as glycol nitriles from solutions of formaldehyde;

the reaction of formaldehyde with olefins in a Prins reaction to give alpha-hydroxymethyl compounds;

condensation reactions of formaldehyde with amines such as aniline or toluidine to form Schiff bases which can react further to give diphenylmethane derivatives such as diphenylmethanediamine;

reaction of hydroxylamine with formaldehyde to form oximes;

reaction of formaldehyde with diols to form cyclic ethers, for example of glycol and formaldehyde to form dioxolane;

conversion into oxymethylene homopolymers or copolymers, for example as described in the German patent application DE 101 58 813.5, which is not a prior publication;

reaction of formaldehyde solutions with alcohols to form ethers such as polyoxymethylene dialkyl ethers, preferably polyoxymethylene dimethyl ethers.

This listing is not exhaustive. Textbooks on organic chemistry and industrial chemistry give further examples of reactions. However, the listing is intended to illustrate, by way of example, the industrial importance of formaldehyde as a synthetic building block in the overall field of organic chemistry. The products obtained include both small tonnage intermediates in the pharmaceuticals or crop protection sectors, e.g. oximes, and large tonnage products such as diphenylmethane derivatives.

The invention is illustrated by the following example.

EXAMPLE

An aqueous formaldehyde solution consisting of 30% by weight of formaldehyde, 69% by weight of water and 1% by weight of methanol is introduced at the top of a liquid-heated laboratory thin film evaporator having an internal diameter of 50 mm and a wiped length of 300 mm. The feed flow is 1 l/h. The heating jacket temperature of the thin film evaporator is set to 120° C. and the pressure in the interior space is set to 100 mbar. The evaporation rate of the apparatus is about $m_D/m_L=3/1$. Under these conditions, an aqueous formaldehyde solution consisting of about 80% by weight of formaldehyde and 20% by weight of water and less than 0.2% by weight of methanol is obtained at the bottom of the thin film evaporator at about 55° C.

The solution produced would be stable for only a few minutes at this temperature. To stabilize this high-concentration solution, it is transferred to a heat exchanger. The heat exchanger used is a coil heat exchanger made of glass and having a jacket length of 400 mm. The length of the coiled tube is 3.2 m, and its internal diameter is 6 mm. The formaldehyde solution is passed through the heat exchanger. The jacket of the apparatus is heated by means of a large stream of triethylene glycol at 130° C. The solution leaves the heat exchanger at 120° C. The heating rate of the tube-side medium achieved under these conditions is about 13° C./min, which is above the required minimum rate of 5° C./min. Under the process conditions described, no precipitation of solids occurs at any point in the apparatus. The formaldehyde solution leaving the heat exchanger is clear and colorless and liquid and can be maintained in a stable condition without precipitation of solids at 120° C. for a prolonged period.

We claim:

1. A method of stabilizing high-concentration formaldehyde solutions having a $CH_2O$ content of >70% by weight against precipitation of solids, which comprises heating the high-concentration formaldehyde solution at a heating rate of at least 5° C./min to a temperature of from 100° C. to 200° C. immediately after it has been prepared and storing it at a temperature in this range.

2. A method as claimed in claim 1, wherein the heating rate is at least 10° C./min.

3. A method as claimed in claim 1, wherein the solution is heated to not more than 150° C.

4. A method as claimed in claim 1, wherein the pH of the high-concentration formaldehyde solution is from 1 to 10.

5. A method as claimed in claim 1, wherein the pH of the high-concentration formaldehyde solution is from 2 to 9.

6. A method as claimed in claim 1, wherein the pH of the high-concentration formaldehyde solution is from 3 to 6.

7. A method as claimed in claim 1, wherein the high-concentration formaldehyde solution is obtained from a formaldehyde solution having a lower concentration in a film evaporator.

8. A method as claimed in claim 2, wherein the solution is heated to not more than 150° C.

9. A method as claimed in claim 8, wherein the pH of the high-concentration formaldehyde solution is from 3 to 6.

10. A method as claimed in claim 9, wherein the high-concentration formaldehyde solution is obtained from a formaldehyde solution having a lower concentration in a film evaporator.

* * * * *